(12) United States Patent
Altarac et al.

(10) Patent No.: US 10,492,836 B2
(45) Date of Patent: *Dec. 3, 2019

(54) ANTERIOR CERVICAL PLATE

(71) Applicant: Centinel Spine, LLC, New York, NY (US)

(72) Inventors: Moti Altarac, Irvine, CA (US); Joey Reglos, Irvine, CA (US)

(73) Assignee: Centinel Spine, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,856

(22) Filed: Jul. 9, 2018

(65) Prior Publication Data
US 2018/0310966 A1    Nov. 1, 2018

Related U.S. Application Data

(63) Continuation of application No. 15/294,530, filed on Oct. 14, 2016, now Pat. No. 10,016,224.

(51) Int. Cl.
*A61B 17/70* (2006.01)
*A61B 17/80* (2006.01)
*A61B 17/86* (2006.01)

(52) U.S. Cl.
CPC ...... *A61B 17/7059* (2013.01); *A61B 17/7058* (2013.01); *A61B 17/80* (2013.01); *A61B 17/8042* (2013.01); *A61B 17/8615* (2013.01)

(58) Field of Classification Search
CPC ...... A61B 17/80–8095; A61B 17/7058; A61B 17/7059
See application file for complete search history.

(56) References Cited

U.S. PATENT DOCUMENTS

| | | | | |
|---|---|---|---|---|
| 8,652,182 B1* | 2/2014 | Walker | ............... | A61B 17/7059 606/295 |
| 10,016,224 B2* | 7/2018 | Altarac | ................ | A61B 17/80 |
| 2003/0060828 A1* | 3/2003 | Michelson | ......... | A61B 17/7059 606/71 |
| 2004/0015169 A1* | 1/2004 | Gause | ............... | A61B 17/8042 606/63 |
| 2004/0039387 A1* | 2/2004 | Gause | ............... | A61B 17/1728 606/86 B |
| 2005/0187552 A1* | 8/2005 | Michelson | ......... | A61B 17/1604 606/295 |
| 2007/0213728 A1* | 9/2007 | Lindemann | ........ | A61B 17/8042 606/279 |
| 2008/0269806 A1* | 10/2008 | Zhang | .................. | A61F 2/4455 606/280 |
| 2010/0016901 A1* | 1/2010 | Robinson | ........... | A61B 17/8042 606/289 |

(Continued)

*Primary Examiner* — Nicholas J Plionis
(74) *Attorney, Agent, or Firm* — Farber LLC (57) ABSTRACT

An anterior cervical plate system is provided. The plate is configured to receive bone screws for attachment to and immobilization of adjacent vertebrae of the spine. The system includes a lock configured to prevent the bone screws from backing out of the plate. The lock includes at least one blocking surface that is movable between a blocked configuration preventing the bone screw from backing out and an unblocked configuration allowing passage of the bone screw. The lock achieves a blocked position in a rotation of less than 90 degrees while maintaining or increasing a low-profile.

3 Claims, 10 Drawing Sheets

(56) References Cited

U.S. PATENT DOCUMENTS

| | | | |
|---|---|---|---|
| 2011/0190770 A1* | 8/2011 | Suh .................. | A61B 17/80 606/70 |
| 2012/0245690 A1* | 9/2012 | Cowan, Jr. ........... | A61F 2/4465 623/17.16 |
| 2013/0023936 A1* | 1/2013 | Altarac .............. | A61B 17/7059 606/279 |

* cited by examiner

FIG. 13

ANTERIOR CERVICAL PLATE

CROSS-REFERENCE TO RELATED APPLICATION

This application is a continuation of co-pending U.S. patent application Ser. No. 15/294,530 filed on Oct. 14, 2016 entitled "Anterior cervical plate" and incorporated herein by reference in its entirety.

FIELD OF THE INVENTION

The present invention relates to medical devices, and in particular, to bone fixation plates used in spinal surgery.

BACKGROUND OF THE INVENTION

Anterior cervical plates are used for a variety of conditions to immobilize, stabilize or align cervical vertebrae. For example, after cervical spinal fusion surgery, cervical plates are used to add strength and rigidity to the adjoined vertebrae. Also, cervical plates secure vertebrae together where an intervening vertebra has been removed or replaced. In other cases, cervical plates are used to correct instability in the cervical spine caused by trauma, tumors, advanced degenerative discs, infection or congenital or acquired deformities.

A typical cervical plate includes an elongated rectangular plate that spans the distance between two or more vertebrae. The plate is curved to match the natural curvature of the spine at the location to which it is attached and bone screws are used to fasten the plate to the vertebral bodies. A pair of apertures is formed at one end of the plate for passing bone screws through and into a first vertebral body to secure the first end of the plate to the first vertebral body. A second pair of apertures is formed at the other end of the plate for passing bone screws through and into a second vertebral body to secure the second end of the plate to the second vertebral body. Thereby, the plate bridges two vertebral bodies. More vertebrae may be connected with a longer plate and a corresponding increased number of bone screw apertures and bone screws inserted therethrough at the intervening vertebral levels.

The cervical spine can be surgically approached anteriorly or posteriorly. In anterior cervical fusion surgery, an incision is made and the spine is approached from the front of the patient. The carotid sheath, muscles, trachea and esophagus are moved laterally to expose the cervical spine. Holes are drilled into the vertebral bodies or self-tapping screws are employed. The cervical plate is properly aligned on the vertebrae for the receipt of mounting screws and the plate is carefully and firmly attached. Sometimes fusion is accompanied by a discectomy in which a herniated disc is removed and a graft device is placed between the vertebral bodies to assist in fusion across levels. The plate may also include a window formed generally at a location between the two pairs of screw apertures through which bone growth progress may be observed. With the plate in position, the vertebrae are held by the plate in desired spatial relationships and orientations relative to each other, pressure is removed from the nerve roots and pain caused by the herniated disc or other condition is relieved.

Over time, the interface between the screws and the bone may present some problems of stability. Due to the anatomical structure of the cervical spine and the extreme anatomical forces that are brought to bear on the skeleton and transmitted to the cervical spine, the screws securing the plate to the spine may vibrate or toggle out of position. Also, the degeneration of vertebral bone quality may result in the screws loosening or becoming dislodged. As a result, bone screws securing the plate to the spine may move or back out of the vertebral body and plate. Due to the relative location to the esophagus and other connective tissue, if the bone screw securing the plate to the cervical spine backs out, the bone screw could impinge on the adjacent tissue and increase pain. Also, loosened screws may result instability of the joint and lead to increased pain for the patient.

Therefore, there is a need to provide a new and improved anterior cervical plate that resists fasteners, such as bone screws, from backing out of the plate and also from being loosened with respect to the plate before migrating out. Not only an improved and effective fastener retaining mechanism is required, but also, its design cannot add undue bulk to the plate. The anterior cervical plate must have a low profile due to the proximity of the implant site to the esophagus, nerves and other sensitive surrounding tissue. It is also preferable to keep the plate as narrow as possible to reduce the chances that the lateral edges rise off from the underlying vertebral body and cause pain where the curvature of the plate does not exactly match the patient's anatomy. Furthermore, there is a need for the anterior cervical plate to withstand anatomical forces and be easily implanted. Also, the screw retaining mechanism must be easily activated by the surgeon. This invention, as described in the detailed description, sets forth an improved anterior cervical plate with anti-back out protection for the bone screws that meets these needs.

SUMMARY OF THE INVENTION

According to another aspect of the invention, a bone plate system is provided. The bone plate system includes a plate having at least one through hole configured to receive a bone screw for attaching the plate to bone. The plate has an upper surface and a lower surface interconnected by side surfaces. The plate includes a lock aperture adjacent to the at least one through hole. The lock aperture is configured to receive a lock at the upper surface. The system further includes a bone screw having a head portion connected to a shank portion. The bone screw is configured for insertion into the through hole. The system further includes a lock having a main body. The lock is connected to the plate such that the lock is permitted to rotate with respect to the plate. The main body of the lock has a top surface and a bottom surface interconnected by a perimeter surface. The lock has an unlocked position in which the main body of the lock does not cover the head of the bone screw inside the through hole permitting passage of the bone screw in or out of the through hole and a locked position in which at least part of the main body is above the head portion of the bone screw to prevent the bone screw from backing out of the through hole. At least part of the perimeter surface of the lock includes a taper.

According to another aspect of the invention, a bone plate system is provided. The bone plate system includes a plate having at least one through hole configured to receive a bone screw for attaching the plate to bone. The plate has an upper surface and a lower surface interconnected by side surfaces. The plate includes a lock aperture adjacent to the at least one through hole. The system further includes a bone screw having a head portion connected to a shank portion. The bone screw is configured for insertion into the through hole. The system includes a lock having a main body. The lock is disposed in the lock aperture and connected to the plate such that the lock is permitted to rotate with respect to the plate between a locked configuration in which the main body of the lock does not cover the head of the bone screw inside the through hole permitting passage of the bone screw in or out of the through hole and a locked position in which at least part of the main body is above the head portion of the bone screw to prevent the bone screw from backing out of the through hole. The main body of the lock has a top surface and a bottom surface interconnected by two sides and two blocking ends. At least one side surface of the plate includes a first scallop extending between the upper surface and the lower surface of the plate. The first scallop is configured to receive a setting pin.

According to another aspect of the invention, a bone plate system is provided. The plate includes at least one through hole configured to receive a bone screw for attaching the plate to bone. The plate has an upper surface and a lower surface interconnected by side surfaces. The plate includes a lock aperture adjacent to the at least one through hole. The lock aperture is configured to receive a lock at the upper surface and configured to receive a lock retainer at the lower surface. The upper surface of the plate includes a recess having a bottom surface. The lock aperture is formed in the location of the recess. The bone plate system further includes a bone screw having a head portion connected to a shank portion. The bone screw is sized and configured for insertion into the through hole. The bone plate system further includes a lock retainer connected to the plate and located inside the lock aperture. The lock retainer has a threaded inner surface. The bone plate system further includes a lock having a main body connected to a threaded post. The post is threadingly connected to the threaded inner surface of the lock retainer such that the lock is permitted to rotate with respect to the plate and, with rotation of the lock, to threadingly translate vertically with respect to the plate. The lock has an unlocked position in which the main body of the lock does not cover the head of the bone screw inside the through hole permitting passage of the bone screw in or out of the through hole and a locked position in which at least part of the main body is above the head portion of the bone screw to prevent the bone screw from backing out of the through hole. Rotation of the lock with respect to the plate from the unlocked position to the locked position simultaneously moves the lock in a direction toward the plate and the main body toward the screw head. Rotation of the lock with respect to the plate from the locked position to the unlocked position simultaneously moves the lock in a direction upwardly away from the plate and the main body away from the screw head.

DETAILED DESCRIPTION OF THE INVENTION

Figure 1:
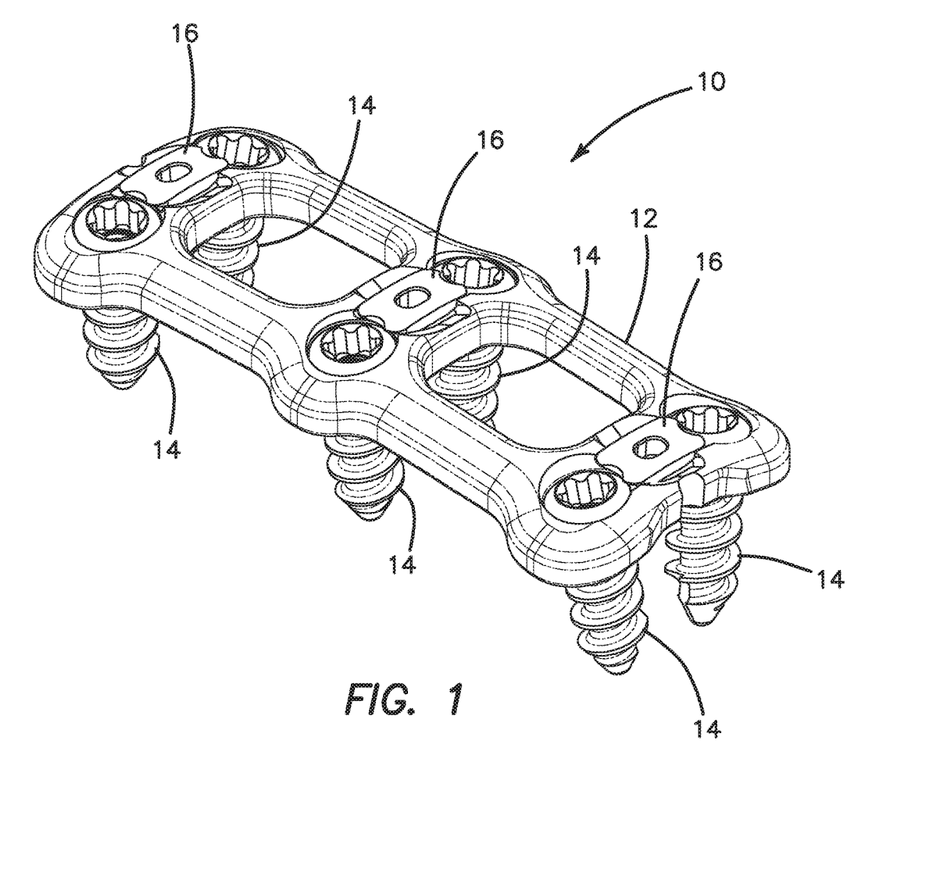
FIG. 1 is a top perspective view of an anterior cervical plate system in a locked position according to the present invention.
Figure 2:
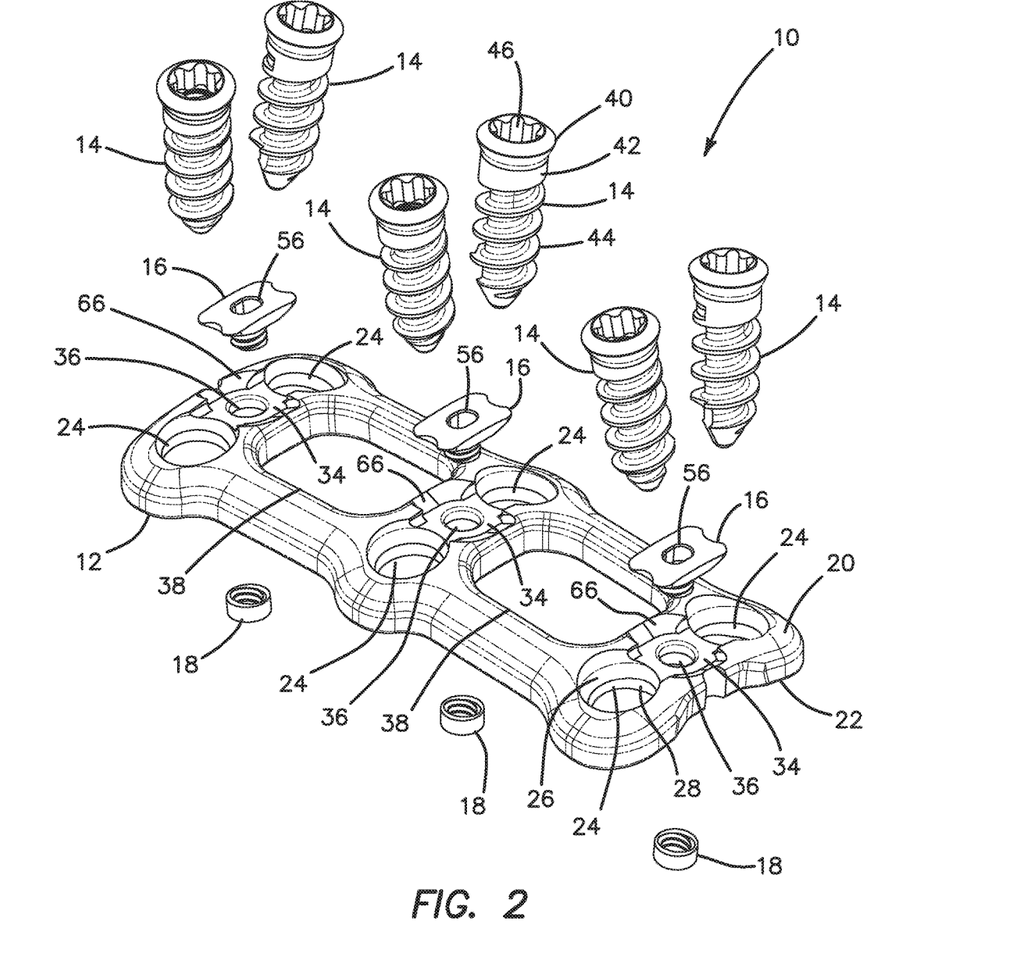
FIG. 2 is a top perspective exploded view of an anterior cervical plate system according to the present invention.

FIGS. 1-2 depict a cervical plate system 10 according to one variation of the invention that may be used to stabilize or fuse vertebral bodies in the cervical or other region of the spine. The anterior cervical plate system 10 that is shown in FIGS. 1-2 is a two-level bone fixation plate that is configured to span across and fixate three vertebrae of the cervical spine; however, the invention is not so limited and the cervical plate system 10 may be a single level or any multilevel anterior cervical plate spanning two or more vertebral bodies and may be used to span any two bone pieces of the human anatomy. The anterior cervical plate system 10 comprises a plate 12 having fasteners 14. The fasteners 14 are prevented from backing out by a lock 16 rotatably connected to the plate 12 with a lock retainer 18.

Figure 3A:
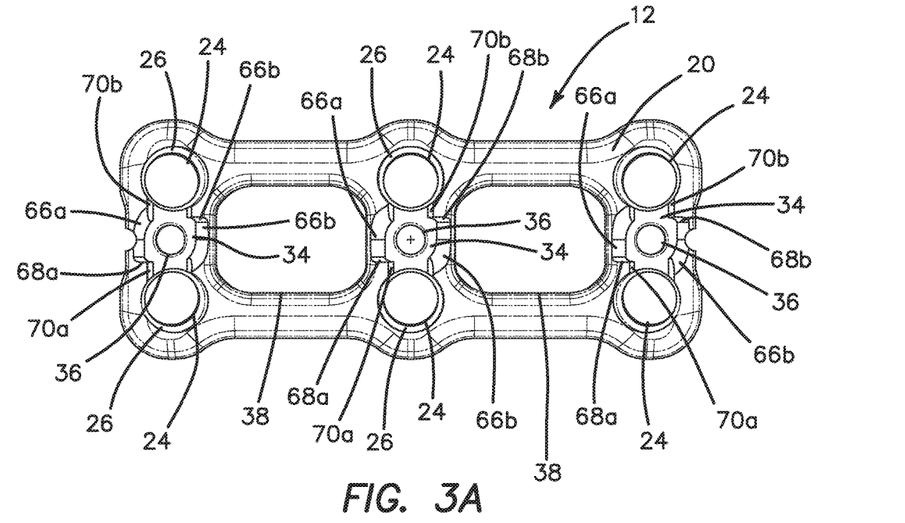
FIG. 3A is a top planar view of the plate according to the present invention.
Figure 3B:
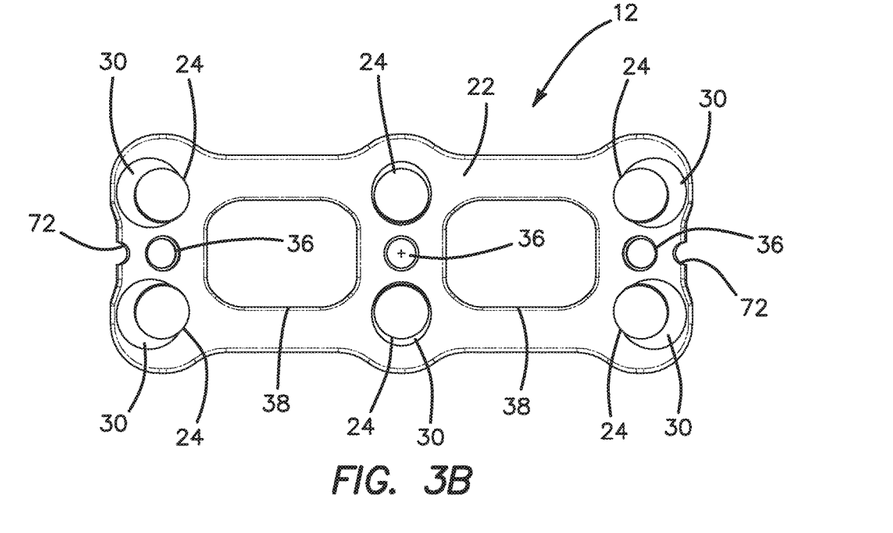
FIG. 3B is a bottom planar view of a plate according to the present invention.
Figure 11:
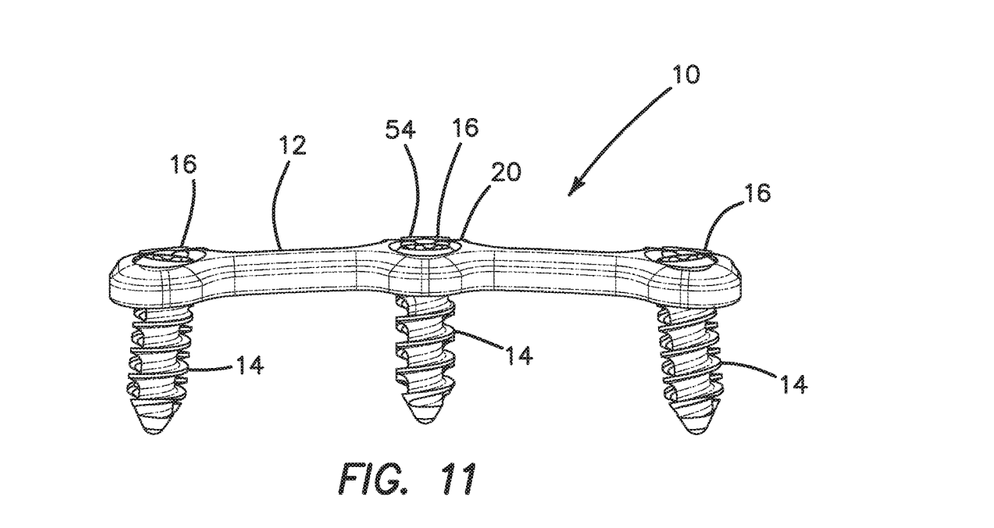
FIG. 11 is a side elevation view of an anterior cervical plate system in a locked position according to the present invention.
Figure 12:
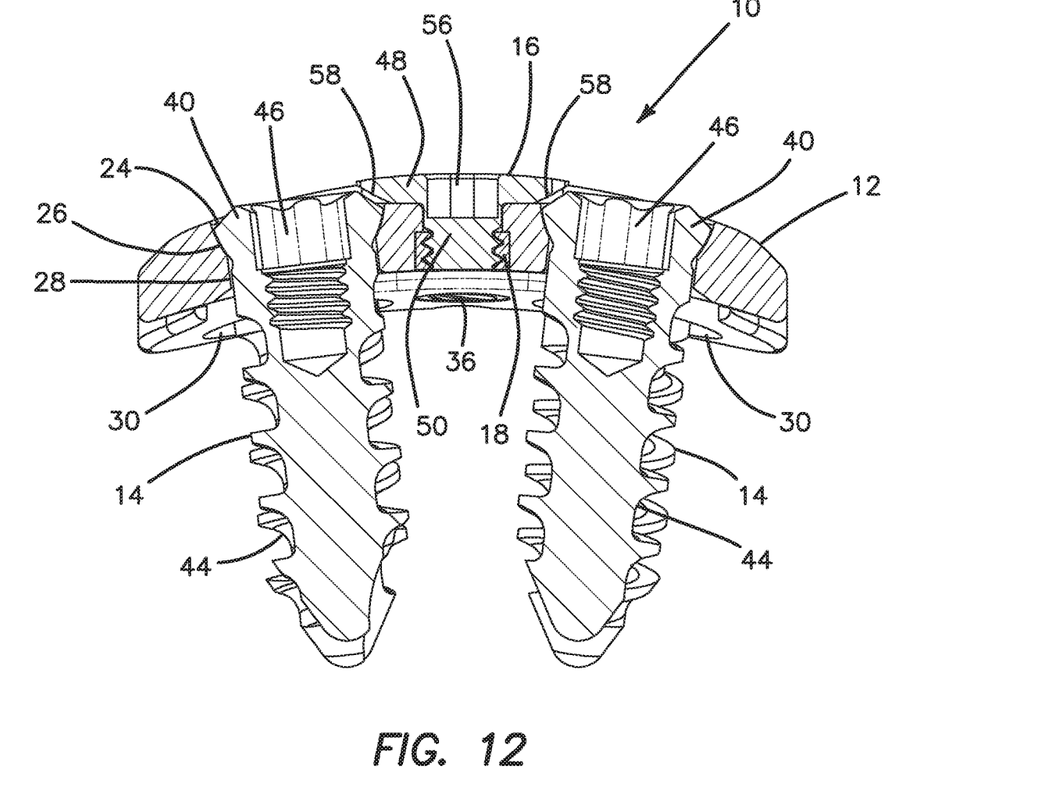
FIG. 12 is a cross-sectional view taken along line 12-12 of FIG. 10 of an anterior cervical plate in a locked position according to the present invention.

With reference to FIGS. 2, 3A and 3B, the plate 12 will now be described in greater detail. The plate 12 includes an upper surface 20 or anterior surface that faces the patient's soft tissue and esophagus when installed and a lower surface 22 or posterior surface facing the vertebral bodies to be immobilized. The upper surface 20 and lower surface 22 are interconnected by curved side walls and end walls to form a generally rectangular shape that is symmetrical about a longitudinal axis of the plate 12. As best seen in FIGS. 8-9 and 11-12, the gently curved structure of the rectangular plate 12 complements the natural curved structure of the vertebral bodies and lordotic curvature of the cervical spine. The corners of the plate 12 are rounded to reduce or eliminate irritation of the esophagus and the surrounding tissue. The plate 12 is sized and shaped for use on an anterior aspect of the cervical spine although one skilled in the art may use the device in other regions of the spine and other skeletal fixations. The plate 12, which resides atop the vertebral bodies, has a low profile as seen in FIG. 12 so as to minimally impinge on adjacent tissues.

The plate 12 and other components of the cervical plate system 10 are made from suitable biocompatible material such as stainless steel, titanium and or any other metal or metal alloy. One or more components may be made of non-metal materials including but not limited to polymer, carbon reinforced polyetheretherketone (PEEK) or one or more biocompatible ceramics. The plate 12 may be additionally configured to promote bone ingrowth to the plate such as a portion of the plate being made of porous material or being roughened by mechanical blasting or plasma spraying with metal particles of one or more sizes. The plate 12 may also be coated with bio-active material, therapeutic agents for enhancing bone fusion and ingrowth, bone morphogenic proteins, growth factors and the like.

Figure 9:
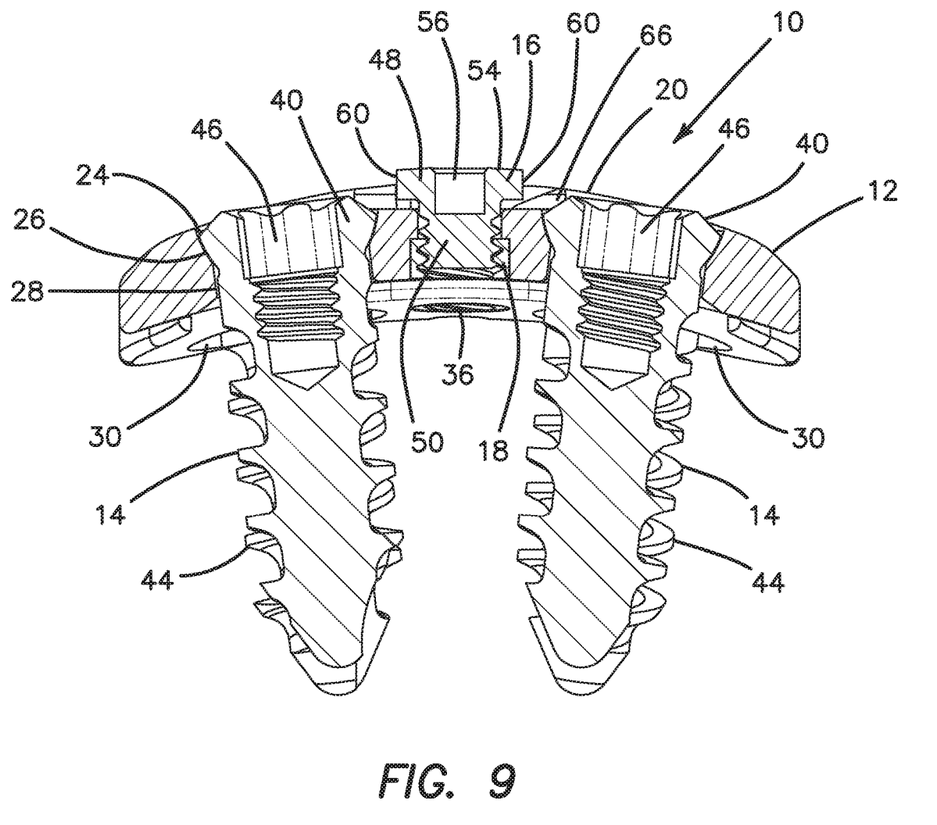
FIG. 9 is a cross-sectional view taken along line 9-9 of FIG. 7 of an anterior cervical plate system in an unlocked position according to the present invention.
Figure 10:
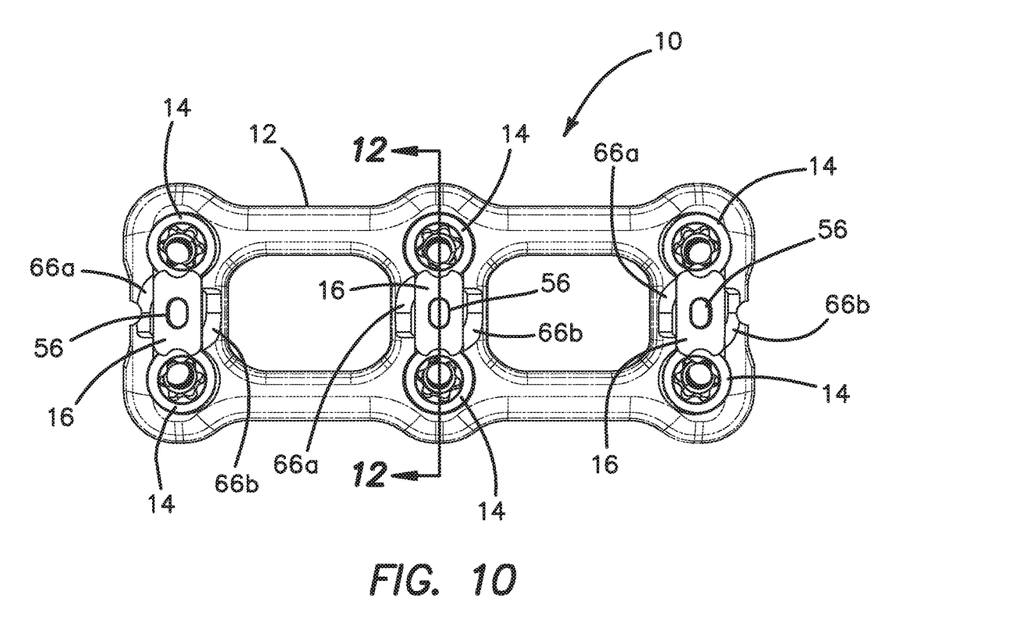
FIG. 10 is a top planar view of an anterior cervical plate system in a locked position plate according to the present invention.

Still referencing FIGS. 2, 3A and 3B, the plate 12 includes a plurality of through holes 24 extending through the cervical plate 12 from the upper surface 20 and through the lower surface 22. The holes 24 are configured to receive bone fasteners 14 passed there through. Each hole 24 includes a head-receiving portion 26 near the upper surface 20 connected to a smaller shank-receiving portion 28 near the lower surface 22 to, thereby, in one variation, provide a seat for the head portion of the fastener 14 such that the head portion of the fastener 14 does not pass distally through the through hole 24. The head-receiving portion 26 is recessed from the top surface 20 as best seen in FIGS. 9 and 12 such that the head of the fastener 14 does not protrude beyond the upper surface 20 of the plate 12 in order to maintain a low profile for the plate 12. Each through hole 24 has a larger exit opening 30 at the lower surface 22 to allow room for the angulation of inserted fasteners 14. The head-receiving portion 26 forms a part-spherical seat or curved surface configured for a complimentary part-spherical or curved outer surface of the head portion of the fastener 14. In one variation, the size of the through hole 24 is configured such that the head-receiving portion 26 and shank-receiving portion 28 are both large enough to allow a bone fastener 14 to pass all the way through the plate without the presence of a retention ring and wherein the presence of the retention ring in the through hole reduces the size of the through hole 24 such that the head portion of the fastener 14 is not allowed to pass through the retention ring.

FIGS. 1, 2, 3A and 3B depict a plate 12 having three sets or three pairs of fastener through holes 24 spaced apart along the plate centerline for driving fasteners 14 into and stabilizing three vertebral bodies for creating a two-level construct. Each set of fastener through holes 24 includes two holes 24 spaced oppositely apart from each other along the centerline of the anterior cervical plate 12. Each set or pair of through holes 24 is adapted for receiving two fasteners 14 to be driven into a single vertebral body.

Figure 6:
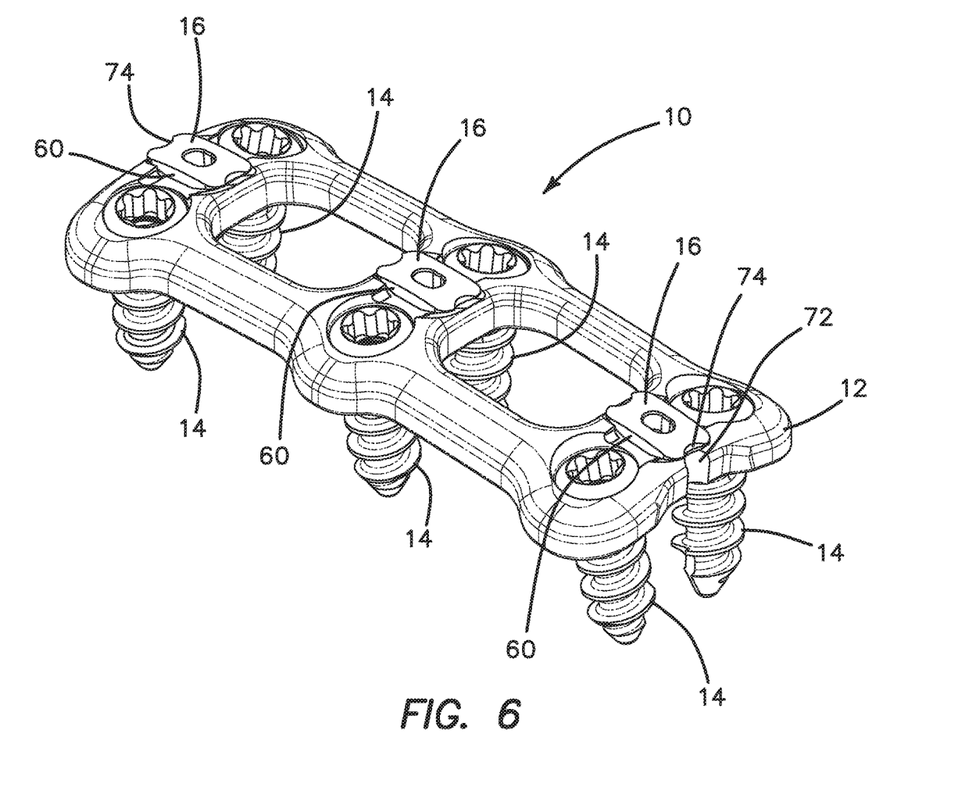
FIG. 6 is a top perspective view of an anterior cervical plate system in an unlocked position according to the present invention.
Figure 7:
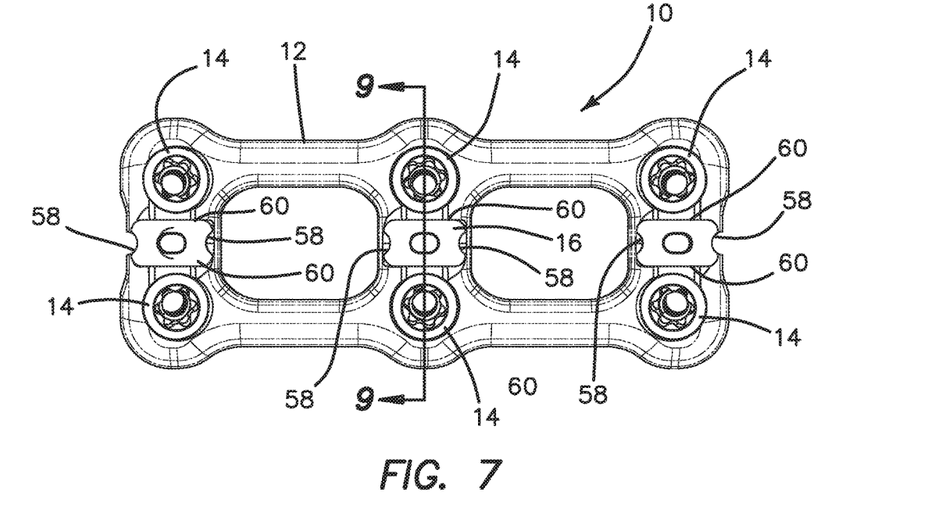
FIG. 7 is a top planar view of an anterior cervical plate system in an unlocked position according to the present invention.

Still referencing FIGS. 2, 3A and 3B, the plate 12 further includes a recess 34 located between the through holes 24 of each pair of through holes 24. The recess 34 is configured for receiving the lock 16 such that the lock 16 does not substantially protrude from the upper surface 20 of the plate 12 when in a locked position in order to maintain the desired low profile as shown in FIGS. 11-12. A lock aperture 36 is formed in the recess 34 at the centerline for coupling the lock 16 to the plate 12. In particular, the lock aperture 36 is sized and configured to receive the lock retainer 18. The plate 12 also includes two larger openings 38 located between each pair of through holes 24 that effectively reduce the overall weight of the plate 12 and provide a visualization pathway to monitor bone graft progress between the vertebral bodies. In one variation, the end walls of the plate 12 include a scallop 72, shown in FIGS. 3B, 6 and 13, that is configured to accommodate a setting pin that a surgeon uses to hold the plate 12 in position against the bone of the patient when inserting the fasteners 14. To accommodate the setting pins, the locks 16 located near the end walls will also have corresponding scallops 74 that align with the scallops 72 in the plate 12 when in the unlocked configuration as shown in FIGS. 4B and 6. In one variation, only the plate 12 has one or more scallop 72. In another variation, only one or more lock 16 has one or more scallop 74. And, in the variation shown in the figures, one or more lock 16 has one or more scallop 74 and the plate 12 has one or more scallop 72.

With continued reference to FIG. 2, an exemplary orthopedic fastener 14 that is preferably used with the cervical plate system 10 of the present invention is a bone screw 14. The bone screw 14 includes a screw head 40, neck 42 and threaded shank 44. The head 40 includes an instrument recess 46 for receiving a complementary tip of a surgical tool. A substantially hexagonal, daisy-shaped recess 46 is shown in FIG. 2, however, the recess 46 can be of any shape that allows a surgical tool to drive the bone screws 14 into the vertebral column. The head 40 of the bone screw 14 corresponds to the shape of the head-receiving portion 26 of the through hole 24. Various bone screws 14 may be employed including ones capable of poly-axial, variable angle or fixed angled orientation with respect to the plate 12 with or without the ability to be locked down at a desired angle or orientation with respect to the plate 12. The bone screws 14 are preferably self-tapping, however, other screws requiring holes to be drilled or pre-tapped can also be employed.

Figure 4A:
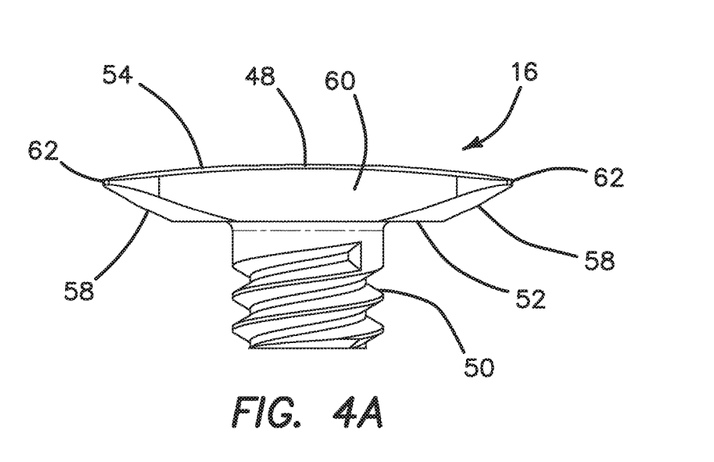
FIG. 4A is a side elevation view of a lock according to the present invention.
Figure 4B:
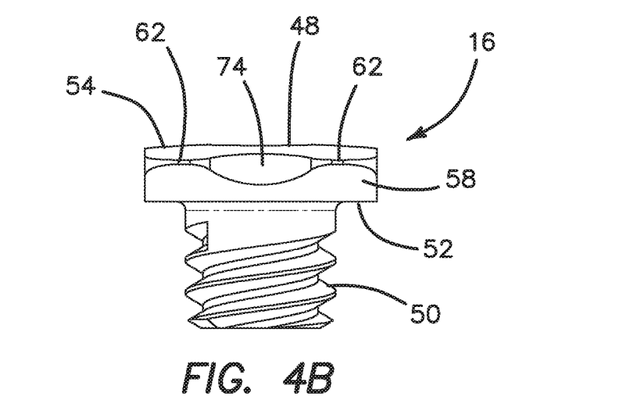
FIG. 4B is an end elevation view of a lock according to the present invention.
Figure 5:
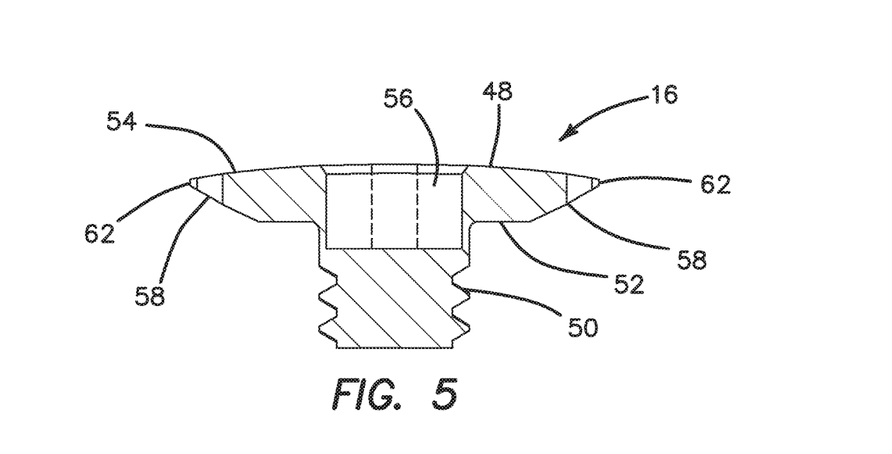
FIG. 5 is a cross-sectional view of a lock according to the present invention.

Turning now to FIGS. 4A, 4B and 5, the lock 16 will now be described. The lock 16 includes a main body 48 connected to a post 50. The post 50 extends from the bottom surface 52 of the main body 48 along the longitudinal axis of the lock 16. The post 50 is configured to be inserted into the lock aperture 36 of the plate 12 and connected to the plate 12 such that the lock 16 can rotate relative to the plate 12 about the longitudinal axis of the post 50. Of course, the lock 16 is not limited to rotational movement with respect to the plate 12 and can be designed for linear movement with respect to the plate 12 for example. Whereas the post 50 is inserted into the plate 12, the main body 48 of the lock 16 resides above the upper surface 20 of the plate 12 in the location of the recess 34 next to a through hole 24 or in another variation as shown in the figures in the location of the recess 34 between two adjacent through holes 24 such that the main body 48 of the lock 16 does not substantially extend beyond the outer profile of the plate 12 maintaining the smooth low profile of the plate 12.

Still referencing FIGS. 4A, 4B and 5 and with reference back to FIG. 1, the main body 48 of the lock 16 will now be described. The main body 48 includes a bottom surface 52 and a top surface 54. The top surface includes a socket 56 shown in FIG. 1 and in cross-section in FIG. 5. The socket 56 is configured to receive an instrument such as a driver having a complementary shaped tip for engaging and rotating the lock 16 between an unlocked position and a locked position. The lock post 50 extends downwardly from the bottom surface 52 of the main body 48. The lock post 50 includes a threaded outer surface configured for threaded engagement with the lock retainer 18 which will be described in greater detail below. The top surface 54 and the bottom surface 52 of the main body 48 are interconnected by two locking ends 58 and two sides 60. The two locking ends 58 and the two sides 60 are generally parallel and opposite to each other and define an elongate, rectangular-like shape when viewed from the top with the two sides 60 having a length that is greater than the length of the two locking ends 58. Although a rectangular or elongate shape is shown in the figures, the main body 48 can have any other suitable shape such as elliptical. As can be seen clearly in FIGS. 4A and 5, the locking ends 58 are angled with respect to the top surface 54 and with respect to the bottom surface 52 such that the top surface 54 is longer in length than the bottom surface 52. The main body 48 is tapered such that the main body 48 becomes narrower and has a reduced area at each of the locking ends 58 with locking end tips 62 being formed near the top surface 54.

Figure 13:
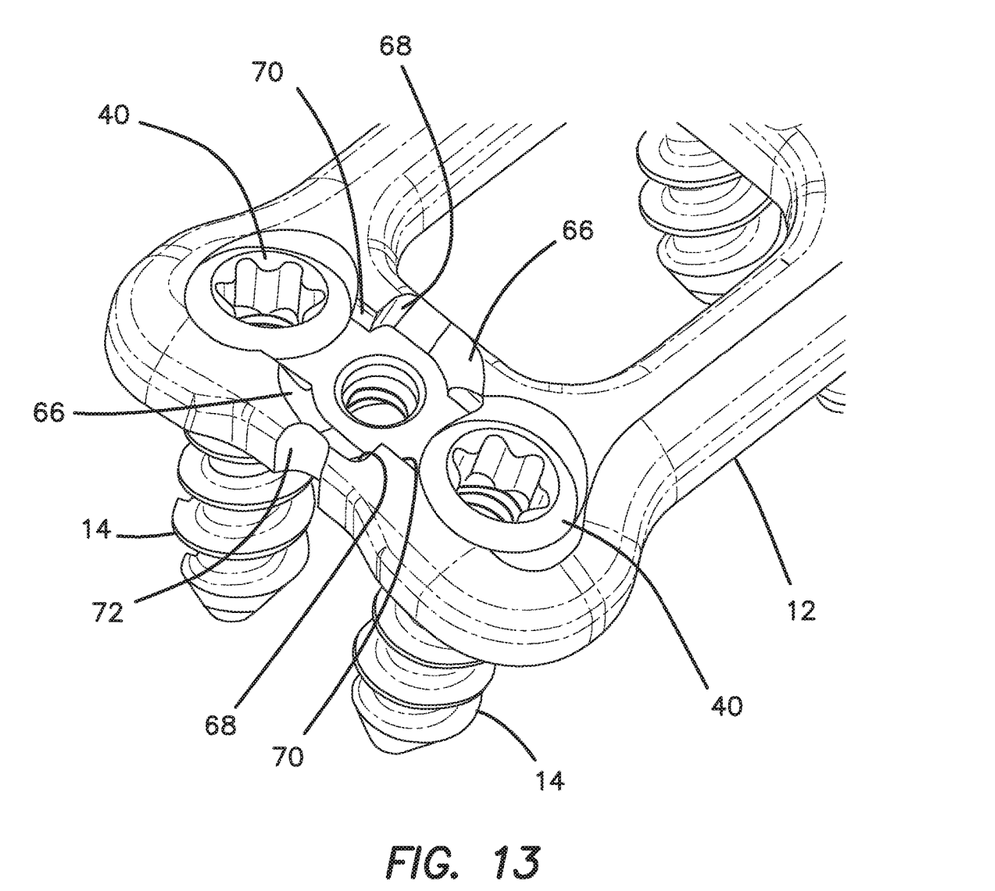
FIG. 13 is a sectional, top perspective view of an anterior cervical plate system without a lock according to the present invention.

With reference to FIGS. 3A and 13, the recess 34 in the top surface 54 of the plate 12 includes at least one ramped surface 66. In particular, in a variation in which the lock 16 is located between two through holes 24 and configured to lock two fasteners 14 in place, the recess 34 includes two oppositely disposed ramped surfaces 66a and 66b. The ramped surfaces 66a, 66b are configured such that they are angled with respect to the base of the recess 34 which is flat in the area immediately surrounding the lock aperture 36 and adjacent to the through holes 24. The ramped surfaces 66a, 66b are angled from the base of the recess 34 at an angle upwardly toward the upper surface 20 of the plate that forms the outer profile. The lock 16 in the recess 34 can rotate approximately 90 degrees from an unlocked configuration shown in FIGS. 6-9 to a locked configuration shown in FIGS. 1 and 10-12. Although a fully locked configuration is shown to be at the end of a 90 degree rotation of the lock 16, actual blocking of the fastener 14 to prevent back-out may take place when the lock 16 rotates less than 90 degrees. For example, the locking ends 58 may start to cover the fasteners 14 and effect a locking condition at a rotation of approximately 45 degrees. In particular, the surfaces of the locking ends 58 will start to cover the top of the screw heads 40 at a rotation of approximately 45 degrees effecting a blocking condition preventing back-out of the fastener 14. In another variation, the lock 16 may cover the fastener 14 preventing back-out and effecting a locking condition in a rotation of as little as approximately 30 degrees from an unlocked configuration.

Each ramped surface 66a, 66b has a first stop 68a, 68b, respectively, at a first end of the ramped surface. The recess 34 also includes second stops 70a, 70b located approximately 90 degrees from the respective first stops 68a, 68b. The first stops 68a, 68b and the second stops 70a, 70b limit the rotation of the lock 16 to approximately 90 degrees and serve as blocking surfaces at zero degrees and at 90 degrees preventing further rotation of the lock 16. The stops 68a, 68b, 70a, 70b are substantially vertically oriented surfaces that are substantially perpendicular to the base of the recess 34.

With reference to the unlocked configuration in FIGS. 6-9, as the lock 16 is rotating from the unlocked configuration, the lock 16 is prevented from rotating counterclockwise by first stops 68a, 68b. These stops 68a, 68b will abut sides 60 of the lock 16. As the lock 16 rotates clockwise 90 degrees, from the unlocked configuration to a locked configuration as depicted in FIGS. 1 and 10-12, the sides 60 of the lock 16 will come to abut the second stops 70a, 70b. Of course, the lock 16 can be configured such that it rotates counterclockwise 90 degrees to a locked configuration and clockwise to an unlocked configuration when viewed from the top and the degree of rotation may be adjusted to be more or less than approximately 90 degrees. The zero and ninety degree positions of lock 16 are fully unlocked and fully locked configurations, respectively. As noted above, the lock 16 is configured such that a rotation of the lock 16 less than 90 degrees will effect a blocked condition of the fasteners 14.

Figure 8:
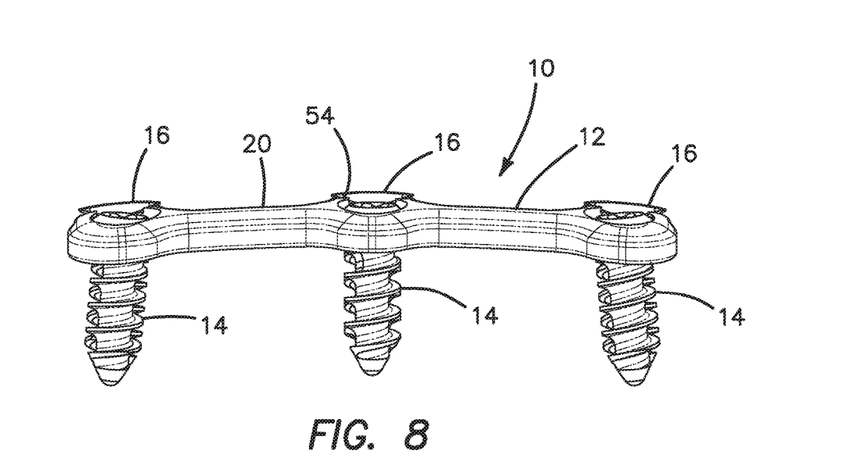
FIG. 8 is a side elevation view of an anterior cervical plate system in an unlocked position according to the present invention.

Furthermore, the lock post 50 is threaded such that rotation of the lock 16 inside the threaded lock retainer 18 from an unlocked configuration to a locked condition will result in the lock 16 being threadingly drawn downwardly into the plate 12 which advantageously helps cover even come closer to the screw head 40 residing in the through hole 24 and with sufficient rotation of the lock 16 will advantageously even contact the screw head 40. Also, when the lock 16 moves from an unlocked configuration to a blocked position, the angled surfaces of the locking ends 60 will move along the ramped surfaces 66a, 66b. When the lock 16 is rotated from a locked condition to the unlocked configuration, the lock 16 moves threadingly upwardly away from the plate 12 and rises above the base of the recess 34. This upward/downward movement of the lock 16 assists in unlocking/locking the fastener 14 because the lock 16 is not only moved laterally with respect to the plate 12 but also along the vertical direction as well. Also, in moving between the unlocked position and blocked position, the lock 16 will move along the ramped surface 66. Because of the threaded engagement with the lock retainer 18, the lock 16 will protrude slightly above the profile of the plate's upper surface 20 and move towards alignment with the profile of the plate's upper surface 20. Therefore, any degree of rotation from the unlocked configuration toward the locked configuration will advantageously progressively reduce the protrusion and reduce the profile of the plate in the vertical direction regardless of the ultimate rotational angle of the resulting locked position which may not be always at 90 degrees. This is illustrated in FIGS. 8-9, where the top surface 54 of the lock 16 is seen above the upper surface 20 of the plate 12 and, in FIGS. 11-12, where the top surface 54 is more flush or completely flush with the upper surface 20 of the plate 12 when in the locked configuration, thereby, advantageously providing a low-profile to the cervical plate system. The lock 16 is configured such that the rotation of one lock 16 will simultaneously effect a locking condition or an unlocked configuration of two fasteners 14 that are oppositely disposed with respect to the lock 16. Of course, the system may be configured such that one lock 16 only locks/unlocks one fastener 14.

With reference to FIGS. 2, 9 and 12, the lock retainer 18 will now be described. The lock retainer 18 is cylindrical in shape having an outer surface and a threaded inner surface defining a central lumen. The lock retainer 18 is sized and configured to threadingly receive the threaded lock post 50 of the lock 16. The lock retainer 18 is also sized and configured to be inserted into the lock aperture 36 formed in the plate 12. In particular, the lock aperture 36 has a larger diameter portion at the lower surface 22 of the plate 12 compared with a smaller diameter portion at the upper surface 20 of the plate 12 as can be seen in FIGS. 9 and 12. As such, the lower larger diameter portion of the lock aperture 36 is sized and configured to receive the lock retainer 18 therein.

The cervical plate system 10 is assembled by first inserting the lock 16 and positioning it in the locked configuration. While the lock 16 is in the locked configuration, the lock retainer 18 is inserted into the lock aperture 36 from underneath the plate 12 at the lower surface 22. Inserting the lock retainer 18 involves threading the lock post 50 of the lock 16 into the threaded inner surface of the lock retainer 18. The lock retainer 18 is fully tightened onto the lock post 50 while the lock 16 is in the locked configuration. When fully tightened in this position, the lock retainer 18 is welded to the plate 18. The lock 16 is connected to the plate 12 via the lock retainer 18 but allowed to rotate with respect to the plate 12 between a blocked condition and an unlocked condition. The lock 16 is also allowed to move in direction perpendicular to the plate, vertically, upwardly and downwardly by a distance permitted by the threaded engagement. When in the lock 16 is positioned in an unlocked configuration the through holes 24 are ready to receive fasteners 14.

In use, the anterior cervical plate 12 according to the present invention is placed or attached adjacent to a vertebral column. The placement of the plate 12 relative to the vertebral bone in a patient may be pre-operatively determined based on a pre-operative examination of the patient's spine using non-invasive imaging techniques known in the art. Any additional preparation or work may be done on and around the desired vertebrae prior to positioning the plate 12. Once the plate 12 is appropriately positioned, it may be necessary to keep the plate 12 in the desired position while inserting fasteners 14. Setting pins may be employed to assist in keeping the plate 12 in position against the bone. When setting pins are used, the scallops 72 in the plate 12 and scallops 74 in the lock 16 are aligned which means that the lock 16 is moved into an unlocked configuration. This position allows the setting pins to be employed as well as permits fasteners to be passed through the through holes 24. The scallops 72, 74 provide a location on the plate system 10 for holding the plate 12 in position against the vertebrae. Next, bone fasteners 14 are inserted into through holes 24 of the plate 12 while the lock 16 is in an unlocked position. To insert a bone fastener 14, an instrument is inserted into the instrument recess 46 of the fastener 14 and the fastener 14 is driven or screwed into the desired bone location. Once the fasteners 14 are correctly positioned in the through holes 24, the lock 16 is rotated from the unlocked configuration towards the locked configuration. To rotate the lock 16, an instrument is inserted into the socket 56 and the lock 16 is rotated from an unlocked position as shown in FIGS. 6-9. Rotation of the lock 16 is only permitted in one direction because of first stops 68a, 68b that abut both sides 60 of the lock 16 from opposite directions. As the lock 16 is rotated, the blocking surfaces of the blocking ends 58 of the main body 48 moves along the ramped surface 66 until the locking ends 58 are in a position above the through holes 24 to cover the screw heads 40 of the inserted fasteners 14. The screw heads 40 of adjacent fasteners 14 are covered simultaneously by one lock 16. When any portion of the bottom surface 52 of the lock 16 covers the screw head 40 at least partially, back-out protection is achieved and a locked condition is effected. The surgeon may choose to continue with the rotation of the lock 16 such that a greater portion of the screw head 40 is covered by the lock 16. However, this is not necessary and sometimes anatomically not possible because positioning of the fastener 14 may result in the fastener 14 being angled with respect to the upper surface of the plate 12 such that a portion of the screw head 40 projects above the plate 12 making it impossible for the lock 16 to further cover the screw head 40. Advantageously, once the screw head 40 is covered by even a little of the locking end 58 further covering of the screw head 40 or completely covering the screw head 40 with further rotation of the lock 16 to even a 90 degree orientation of the lock 16 is not necessary with the present invention and rotation of the lock 16 may be terminated. The angled locking ends 58 advantageously further provide additional clearance for covering the screw head 40 without having a full thickness of the main body interfering with blocking a protruding screw head. This is especially useful in the case of a slightly protruding fastener 14. The tips 62 of the lock 16 enable the lock 16 to rotate further towards the locking configuration and, in effect, reach over the screw head 40 and/or through holes 24 more than if the bottom surface 52 was not angled or not tapered at the locking ends 58 of the lock 16. It is up to the surgeon's discretion to determine if the lock 16 is adequately positioned to prevent the backing out of the fasteners 14. In some circumstances, the surgeon may choose to rotate the lock 16 more and even all the way to the locked configuration wherein the sides 60 of the lock 16 abut the second blocking surfaces 70a, 70b. The surgeon may opt to move the lock into an unlocked configuration and further drive the bone screw deeper into the bone such that the screw head 40 is more recessed and then rotate the lock closer to a 90 degree position. The locked condition prevents the bone screw 14 from loosening before migrating back out of the through hole 24 and keeps the bone screw 14 inside the through hole 24. When all of the fasteners 14 are inserted and in position, the setting pins are removed and all of the locks 16 are turned to their locked conditions and the surgical procedure is finalized.

To remove the bone plate 12 from a patient, the same instrument is used to rotate the lock 16 from the locked position to the unlocked configuration in which the locking ends 58 are not adjacent or covering the fasteners 14. Then an instrument can be inserted into the instrument recess 46 on the screw head 40 to remove the bone screws 14. The instrument is used to back out the screw 14.

The anterior cervical plate system 10 of the present invention provides several advantages over previous designs. For example, the lock translates vertically with respect to the plate. In particular, the main body of the lock moves downwardly with respect to the plate such that the top surface 54 of the lock becomes increasingly flusher with the top surface of the plate when in the locked configuration compared with the unlocked configuration where it stands more proud. This vertical movement of the lock advantageously results in a lower profile configuration that reduces impingement of the plate system on the surrounding tissue and nerves. Other locks only move laterally with respect to the plate while maintaining the same height. In the present invention, the lock changes height which permits even thinner plates to be made. Furthermore, in the present invention, the lock changes height with rotation of the lock. When the lock is moving into a locked configuration it advantageously simultaneously decreases in height. This decrease in height allows the locking ends of the lock to come closer to the screw head and even contact and press upon the screw with variable, adjustable force. For example, the amount of force applied on the patient is conveniently adjustable by the surgeon based on the surgeon's discretion with respect to the anatomy and the patient's condition. For example, a surgeon, who knows that a patient has brittle bone or a difficult anatomy, can decide not to rotate the lock all the way to the 90 degree position if such rotation would result in the application of increased force upon the anatomy. Also, rotation of the lock progressively increases the force that the lock exerts on the screw head. In previous devices, the same amount of force is required to move a lock into a locked condition without respect to the patient's anatomy. Also, if the patient's anatomy requires a highly-angled placement of the bone fastener or if the bone fastener cannot be driven deeply into bone, the present invention permits such placement of the fastener and still allows the back-out protection to be employed by the user by rotating the lock less than 90 degrees to cover only the lower surface of the angled screw head instead of covering the entire screw head as in previous devices, or being able to cover a more proud placement of the screw head because of the locks advantageous change in height. Furthermore, as the lock moves down it may contact the screw head in a locked condition. As a result, the screw is prevented from toggling in a space between the screw head and the lock which may result in the future loosening of the screw relative to the bone. Previous devices that do not change in height may create a space between the screw head and the lock allowing the bone screw to toggle in a locked configuration. Likewise, when unlocking the device, in the present invention, the screw head moves upwardly to create a clearance for the removal or easy adjustment of the bone fastener. In previous devices, if a threaded portion of the lock is employed, another element is employed to then cover the fastener. Advantageously, in the present invention, the same threaded element effects a blocking condition directly without requiring additional pieces to then in turn effect a lock by those additional pieces covering the fasteners. Although a threaded portion may be used, this threaded portion does not effect a vertical motion of the blocking mechanism. Previous devices also require the bone screw to be driven into bone perfectly such that the screw head is seated beneath the upper surface of the plate within a through hole in order to permit the anti-back-out lock to cover the lock. The perfect positioning of a bone fastener is very difficult and previous devices would require the surgeon to readjust the placement of the bone screw in the bone in order to have the anti-back-out locking mechanism work. In contrast, in the present invention, even an angled screw head can be block partially by a less-than-90-degree rotation of the lock. Also, the main body of the lock of the present invention is advantageously tapered such that there is less volume of the main body to interfere with a bone fastener thereby being able to more easily move into a locked condition. The taper creates a forgiving lock that permits the extra space resulting from the taper to be taken advantage of with the screw head being wedged into the space created by the taper. The present invention sets forth a novel plate system with a number of advantages that include a lower profile and less impingement on surrounding tissue, a locking condition that can be effected more easily and in greater anatomical conditions, and the variable use of force that results in a plate system that is high in respect for tissue.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above.

We claim:
1. A bone plate system, comprising:
a bone screw having a head portion connected to a shank portion;
a plate having at least one through hole configured to receive the bone screw for attaching the plate to bone;
the plate having an upper surface and a lower surface interconnected by side surfaces;
the plate includes a lock aperture adjacent to the at least one through hole;
a lock having a main body;
the lock being disposed in the lock aperture and connected to the plate such that the lock is permitted to rotate with respect to the plate between a locked configuration in which the main body of the lock does not cover the head of the bone screw inside the at least one through hole permitting passage of the bone screw in or out of the at least one through hole and a locked position in which at least part of the main body is above the head portion of the bone screw to prevent the bone screw from backing out of the at least one through hole;
the main body of the lock having a top surface and a bottom surface interconnected by two sides and two blocking ends;
wherein at least one side surface of the plate includes a first scallop extending between the upper surface and the lower surface of the plate;
the first scallop being sized and configured to receive a setting pin; and
wherein the lock includes a second scallop extending between the top surface and the bottom surface of the lock, the second scallop being sized and configured to receive a setting pin, wherein the first and second scallops are aligned when the lock is in the unlocked configuration.
2. The bone plate system of claim 1 wherein the blocking ends of the lock are tapered.
3. The bone plate system of claim 1 wherein the second scallop is formed in at least one of the blocking ends of the lock.

* * * * *